(12) United States Patent
Caranoni et al.

(10) Patent No.: US 9,604,888 B2
(45) Date of Patent: Mar. 28, 2017

(54) PROCESS AND APPARATUS FOR PRODUCING OLEFINS WITH HEAT TRANSFER FROM STEAM CRACKING TO ALCOHOL DEHYDRATION PROCESS

(75) Inventors: Laurent Caranoni, Cabries (FR); Bernard Descales, Marseilles (FR); Neil Turnbull, Fife (GB); Vaughn Clifford Williams, Midlothian (GB)

(73) Assignee: INEOS EUROPE AG, Vaud (CH)

( * ) Notice: Subject to any disclaimer, the term of this patent is extended or adjusted under 35 U.S.C. 154(b) by 364 days.

(21) Appl. No.: 14/124,757

(22) PCT Filed: Jun. 26, 2012

(86) PCT No.: PCT/EP2012/062305
§ 371 (c)(1),
(2), (4) Date: Dec. 9, 2013

(87) PCT Pub. No.: WO2013/004544
PCT Pub. Date: Jan. 10, 2013

(65) Prior Publication Data
US 2014/0114104 A1  Apr. 24, 2014

(30) Foreign Application Priority Data
Jul. 7, 2011  (EP) .................................... 11173055

(51) Int. Cl.
*C07C 4/04* (2006.01)
*C07C 2/06* (2006.01)
(Continued)

(52) U.S. Cl.
CPC ................. *C07C 2/06* (2013.01); *C07C 1/24* (2013.01); *C07C 4/04* (2013.01); *C10G 9/26* (2013.01);
(Continued)

(58) Field of Classification Search
CPC .. C07C 4/00; C07C 4/02; C07C 4/025; C07C 4/04; C07C 4/06; C07C 4/08
(Continued)

(56) References Cited

U.S. PATENT DOCUMENTS 4,097,544 A  6/1978  Hengstebeck
4,232,179 A * 11/1980  Valladares Barrocas . C07C 1/24
585/639

(Continued)

OTHER PUBLICATIONS

Ren, T., et al; "Olefins from conventional and heavy feedstocks: Energy use in steam cracking and alternative processes"; *Energy*, vol. 31, pp. 425-451 (2006) XP-002665213.
(Continued)

*Primary Examiner* — Sharon Pregler
(74) *Attorney, Agent, or Firm* — Nixon & Vanderhye P.C.

(57) ABSTRACT

Method of producing ethylene and, optionally, propylene by subjecting a feedstock to steam cracking to produce a first olefin containing stream; heating an ethanol containing stream with heat from a steam cracker; passing the heated ethanol containing stream over a dehydration catalyst at a temperature between 200 C to 500 C preferably 250 C to 450 C to produce a second olefin containing stream; and combining the first and second olefin containing streams to give an initial product stream containing ethylene and optionally propylene. The initial product stream is subjected to purification including at least i) water content reduction ii) hydrogen content reduction iii) reduction of content of molecules containing 4 or more carbon atoms and iv) ethane content reduction.

19 Claims, 6 Drawing Sheets

(51) Int. Cl.
*C10G 9/26* (2006.01)
*C07C 1/24* (2006.01)

(52) U.S. Cl.
CPC ... *C10G 2300/807* (2013.01); *C10G 2400/20* (2013.01); *Y02P 30/10* (2015.11)

(58) Field of Classification Search
USPC ................................. 585/638, 639, 640, 641
See application file for complete search history.

(56) References Cited

U.S. PATENT DOCUMENTS

| | | | |
|---|---|---|---|
| 4,720,293 | A | 1/1988 | Rowles et al. |
| 5,626,034 | A | 5/1997 | Manley et al. |
| 5,634,354 | A | 6/1997 | Howard et al. |
| 5,763,725 | A * | 6/1998 | Choudhary ............. C07C 4/025 585/648 |
| 5,972,206 | A | 10/1999 | Lenglet et al. |
| 7,041,271 | B2 | 5/2006 | Drnevich et al. |
| 8,884,089 | B2 * | 11/2014 | Chewter .................. C01B 3/24 518/700 |
| 2004/0122275 | A1 * | 6/2004 | Levin ........................ C07C 1/20 585/639 |
| 2011/0005970 | A1 | 1/2011 | Ou et al. |

OTHER PUBLICATIONS

Arvidsson, M., et al; "Process integration study of a biorefinery producing ethylene from lignocellulosic feedstock for a chemical cluster"; *Chalmers University of Technology*, Goteborg, Sweden, pp. 1-99 (2011) XP002665214.

* cited by examiner

US 9,604,888 B2

PROCESS AND APPARATUS FOR PRODUCING OLEFINS WITH HEAT TRANSFER FROM STEAM CRACKING TO ALCOHOL DEHYDRATION PROCESS

This application is the U.S. national phase of International Application No. PCT/EP2012/062305 filed 26 Jun. 2012 which designated the U.S. and claims priority to European Patent Application No. 11173055.2 filed 7 Jul. 2011, the entire contents of each of which are hereby incorporated by reference.

This invention relates to a process and apparatus for producing olefins. More especially the invention relates to a process and apparatus for producing ethylene and/or propylene.

BACKGROUND OF THE INVENTION

Ethylene is a major industrial commodity. A major source of it is steam cracking of saturated hydrocarbons. US 2011/0112314 describes a process for the production of ethylene in which an ethane containing feed is subjected to a cracking to produce ethylene and hydrogen. At least some of the hydrogen is reacted with carbon dioxide and/or carbon monoxide to form oxygenates which are then converted to olefin. It is also known to make ethylene by dehydration of ethanol. In addition, there are many other routes to olefins as illustrated in FIG. 3 of Tao Ren et al publication "Olefins from conventional and heavy feedstocks: . . . " Energy 31 (2006) p 425-451. FIG. 3 clearly illustrates ethanol dehydration as a separate route to olefins as opposed to the steam cracking (SC) conventional route from a range of hydrocarbon feedstocks. Furthermore Ren describes in section 6.2 the latest developments in Naphtha cracking and in section 7.2 advanced olefins production via emerging catalytic olefin technologies wherein the combination of ethanol dehydration and steam cracking processes as an integrated scheme is not described nor is this mentioned as a potential means of reducing the overall energy footprint per tonne of olefin production.

Propylene is almost as significant an industrial commodity. It is obtained by a variety of routes including cracking. It is known also to prepare propylene by metathesis of other olefins such as ethylene and butene mixtures.

Steam cracking is a dominant route for producing olefin products, such as ethylene and propylene with these products being produced at very high purity such that they are suitable for use in polymerisation to polymers such as polyethylene and polypropylene. The purity requirements are extensive, an example would be the purity specification required for Aethylene Rohrlietungsgesellschaft ("the ARG company"), the operator of a common ethylene pipeline across parts of Europe supplying many ethylene polymerisation plants.

TABLE A

Key specifications for ARG ethylene

| Component | Specification |
| --- | --- |
| Ethylene | 99.9% volume minimum |
| Methane & ethane | 1000 ppm volume max |
| Ethane | 500 ppm volume max |
| Acetylene | 2 ppm volume max |
| C3+ | 10 ppm volume max |
| Hydrogen | 10 ppm volume max |
| Water | 10 ppm volume max |

TABLE A-continued

Key specifications for ARG ethylene

| Component | Specification |
| --- | --- |
| Carbon monoxide | 2 ppm volume max |
| Carbon Dioxide | 5 ppm volume max |
| Oxygen | 5 ppm volume max |

TABLE B

Key specifications for typical Polymer grade propylene

| Component | Specification |
| --- | --- |
| Propylene | 99.6% volume minimum |
| Total paraffin | 0.3% volume max |

Residual other key components for polymer grade propylene are similar to those listed for ethylene with similar or lower specification levels.

Unless otherwise qualified proportions of gases as used herein are by volume as measured at STP.

A problem with known ethanol dehydration processes is that they are not totally selective for ethylene. As described in WO2010146332 one of the problems in preparing ethylene from ethanol is that C4 compounds, including C4 olefins, are also produced. For many applications it is necessary to remove these C4 compounds but it is expensive and complex to do so. In many cases the simplest and cheapest recovery schemes only provide a C4 stream suitable for use as a fuel for the process. Ethanol dehydration is a well known technology and much effort recently has focused on improvements to standalone dehydration process schemes for converting ethanol to ethylene, one such being the SINOPEC-ETO process described and illustrated as FIG. 3 by Teng in "New Olefin production technologies in SINOPEC SRIPT" Proceedings—World Petroleum Congress, 2008 19th( ):teng/1-teng/10 coden: wpcpau; issn: 0084-2176 wherein catalyst improvements are being sought to minimise the co-product yield and the fractions lost as Heavy Ends and Light Ends. The typical ethanol selectivity to ethylene and side products from a commercial catalyst is provided in prior art document "Ethylene from Ethanol" process brochure from Chematur Engineering Group on web address; www.weatherlyinc.com/sok/download/Ethylene_rev_0904.pdf

SUMMARY OF THE INVENTION

It has now been surprisingly found that by combining steam cracking with ethanol dehydration in a particular manner an improved synergistic process is obtained. Hitherto it has not been considered possible to combine steam cracking with ethanol dehydration. The presence of oxygenates such as the typical 1% of unconverted ethanol and fractions of % of acetaldehyde leaving a dehydration reactor and entering a steam cracker quench system leads to the recycling of the ethanol via the dilution steam system into the pyrolysis coils causing fouling and undesirable oxygenate species formation during cracking. This combined with the high acetaldehyde loading from dehydration would then pass into the cracked gas compression train and caustic wash system where it was believed that these aldehyde by-products from the ethanol dehydration would polymerise to form red oil in the steam cracker caustic tower thereby causing plugging and fouling. It has now been found that these materials can be removed by washing the ethylene rich gas product before blending it with the olefin containing stream produced from steam cracking of conventional hydrocarbon feedstocks such as naphtha, light alkanes (C2-C4), or gasoil just prior to or within the compression train.

Once it is realised that it is possible to combine the two processes powerful synergic benefits emerge. By combining a dehydration reaction step with conventional steam cracking particular capital cost advantages and better utilisation of side products can be achieved in the production of olefins such as ethylene, propylene and butenes.

According to the invention there is provided a method of producing at least one of ethylene and propylene comprising
a) subjecting a feedstock to steam cracking to produce a first olefin containing stream;
b) heating an ethanol containing stream with heat from a steam cracker;
c) passing the heated ethanol containing stream over a dehydration catalyst to produce a second olefin containing stream; and
d) combining the first and second olefin containing streams to give a product comprising at least one of ethylene and propylene. In some embodiments the second olefin containing stream is washed to reduce the aldehyde content thereof prior to combination with the second olefin containing stream. The combined olefin containing streams can be subjected to further purification. The combined olefin stream can be separated into an ethylene containing stream and a propylene containing stream. Some embodiments of the invention provide a method of producing at least one of ethylene and propylene comprising
a) subjecting a feedstock to steam cracking to produce a first olefin containing stream;
b) subjecting an ethanol containing feedstock to dehydration over a catalyst to produce a second olefin containing stream;
c) washing the second olefin containing stream to reduce the aldehyde content thereof; and
d) combining the first olefin containing stream and the washed second olefin containing stream to give a product comprising at least one of ethylene and propylene. The first and second olefin streams can be combined within a compression stage, preferably between the 1st and 3rd stages of a multistage compressor. The streams can be combined after compression but prior to caustic washing. The olefin streams can be combined after caustic washing but before water removal. According to the invention there is further provided apparatus for producing at least one of ethylene and propylene, the apparatus comprising
i) a steam cracker for cracking a feedstock to produce a first olefin containing stream the steam cracker comprising at least one pyrolysis furnace for heating the feedstock and steam to produce at least one of ethylene and propylene with each furnace incorporating a convection section for recovering heat in the flue gas exiting the combustion section of the pyrolysis furnace;
ii) a dehydration reactor for dehydrating ethanol to produce a second olefin containing stream;
iii) means for reducing aldehyde content of the second olefin containing stream to produce a third olefin containing stream;
iv) means for combining the first and third olefin containing streams to produce a fourth olefin containing stream; and
v) means for purifying the fourth olefin containing stream to produce at least one of ethylene and propylene. In some embodiments the dehydration reactor is situated in the convection section of the steam cracker. According to the invention there is further provided apparatus for producing at least one of ethylene and propylene, the apparatus comprising
i) a steam cracker for cracking a feedstock to produce a first olefin containing stream the steam cracker comprising at least one pyrolysis furnace for heating the feedstock and steam to produce a first olefin containing stream with each furnace incorporating a convection section for recovering heat in the flue gas exiting the combustion section of the pyrolysis furnace;
ii) a dehydration reactor for dehydrating ethanol to produce a second olefin containing stream located in the convection section;
iii) means for combining the first and second olefin containing streams to produce a third olefin containing stream; and
v) means for purifying the third olefin containing stream. The apparatus may further comprise means for reducing the aldehyde content of the second olefin containing stream before combination with the first olefin containing stream.

The invention yet further provides a method of producing ethylene and, optionally, propylene comprising
a) subjecting a feedstock to steam cracking to produce a first olefin containing stream;
b) heating an ethanol containing stream with heat from a steam cracker;
c) passing the heated ethanol containing stream over a dehydration catalyst at a temperature between 200 C to 500 C preferably 250 C to 450 C to produce a second olefin containing stream;
d) combining the first and second olefin containing streams to give an initial product stream comprising ethylene and optionally propylene; and
e) subjecting the initial product stream to purification comprising at least
i) water content reduction
ii) hydrogen content reduction
iii) reduction of content of molecules containing 4 or more carbon atoms and
iv) ethane content reduction. In some embodiments at least one and preferably both of the first olefin containing stream and the second olefin containing stream are additionally subject to water content reduction prior to combination. In some embodiments in step e) the water content of the initial product stream is reduced to less than 10 ppm (by volume at STP) and/or the ethane content of the initial product stream is reduced to less than 500 ppm (by volume at STP) and/or the hydrogen content of the initial product stream is reduced to less than 10 ppm (by volume at STP) and/or the content of molecules containing 4 or more carbon atoms is reduced to less than 10 ppm (by volume at STP). The second olefin containing stream can be treated to reduce the aldehyde content thereof prior to combination with the first olefin containing stream. The invention further provides a method of producing ethylene and propylene comprising producing a final product stream consisting essentially of propylene and ethylene by a method of the invention and separating the final product stream into an ethylene containing stream and a propylene containing stream. The first and second olefin streams can be combined within a compression stage of a compressor at a pressure within the range 0.15 MN/m2 to 3.5 MN/m2 preferably 0.15 MN/m2 to 1.8 MN/m2 for example between the 1st and last or 1st and 5th or 1st and 4th stages of a multistage compressor. In some embodiments the first and second olefin streams are combined within the compressor and prior to a caustic washing step. The invention yet further provides a method of preparing a polymer or copolymer of ethylene comprising the steps of preparing at ethylene and optionally propylene by a method according to the invention and polymerising it optionally in the presence of one or more other polymerisable monomers. The invention further provides apparatus for producing at ethylene and, optionally, propylene, the apparatus comprising i) a steam cracker for cracking a feedstock to produce a first olefin containing stream, the steam cracker comprising at least one pyrolysis furnace for heating the feedstock and for heating steam to produce at least one of ethylene and propylene with each furnace incorporating a convection section for recovering heat in the flue gas exiting the combustion section of the pyrolysis furnace;

ii) a dehydration reactor for dehydrating ethanol comprising to produce a second olefin containing stream;

iii) means for combining the first and second olefin containing streams to produce an initial product stream; and v) purifying means for purifying the initial product stream to produce a final product stream comprising ethylene and optionally propylene the purifying means comprising at least 1) a cooler for cooling the initial product stream to a temperature below 20 C preferably below 15 C so as to produce liquid water which can be separated from the initial liquid stream;

2) a pressure swing absorber and/or palladium and/or platinum membrane and/or a cryogenic distillation column for separating at least some hydrogen from the initial product stream;

3) a distillation column for removing at least some molecules containing 4 or more carbon atoms from the initial product stream; and 4) a cooler for cooling the initial product stream and a distillation column arranged to give an ethylene rich-ethane poor fraction and an ethylene poor-ethane rich stream and for separating the ethylene rich-ethane poor stream from the ethylene poor ethane-rich. The apparatus may further comprise a molecular sieve drier downstream of the cooler 1) for removing further water from the initial product stream. In some embodiments wherein the dehydration reactor is situated in the convection section of the steam cracker pyrolysis furnace. The apparatus may further comprise means for reducing the aldehyde content of the second olefin containing stream before combination with the first olefin containing stream. The invention yet further provides apparatus for producing a polymer or copolymer of ethylene and optionally propylene and/or other polymerisable monomers the apparatus comprising apparatus for preparing ethylene and optionally propylene according to the invention and a reactor for polymerising the ethylene and optionally propylene and/or other polymerisable monomers.

BRIEF DESCRIPTION OF THE DRAWINGS

Embodiments of the invention will be described by way of non-limiting example by reference to the accompanying figures of which

DETAILED DESCRIPTION OF THE INVENTION

Figure 1:
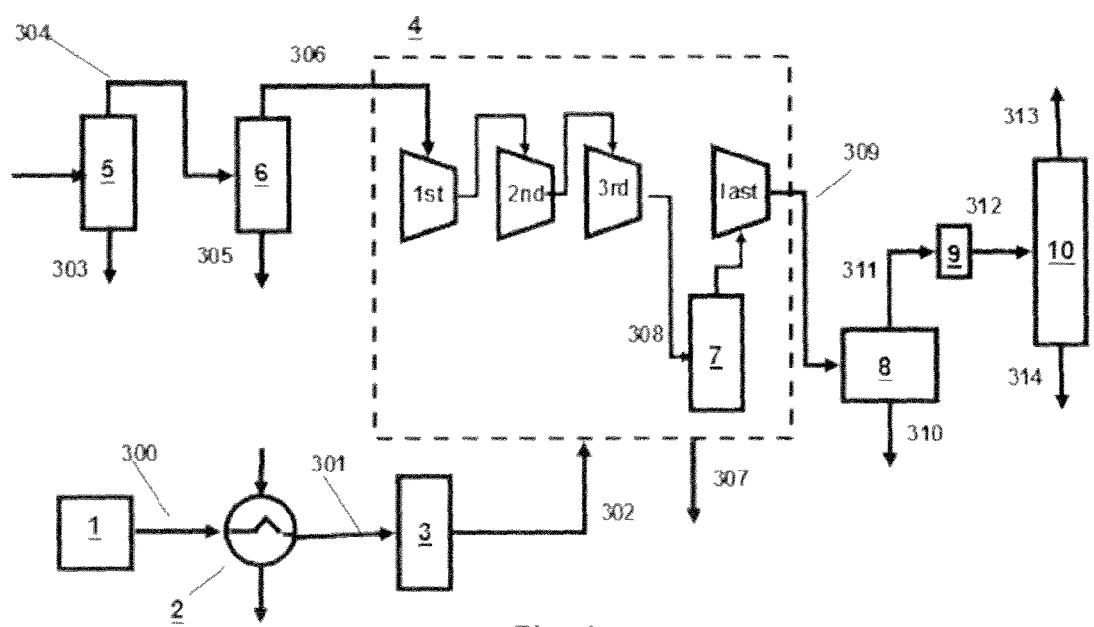
FIG. 1 is a flow sheet showing a part of the process of the invention
Figure 2:
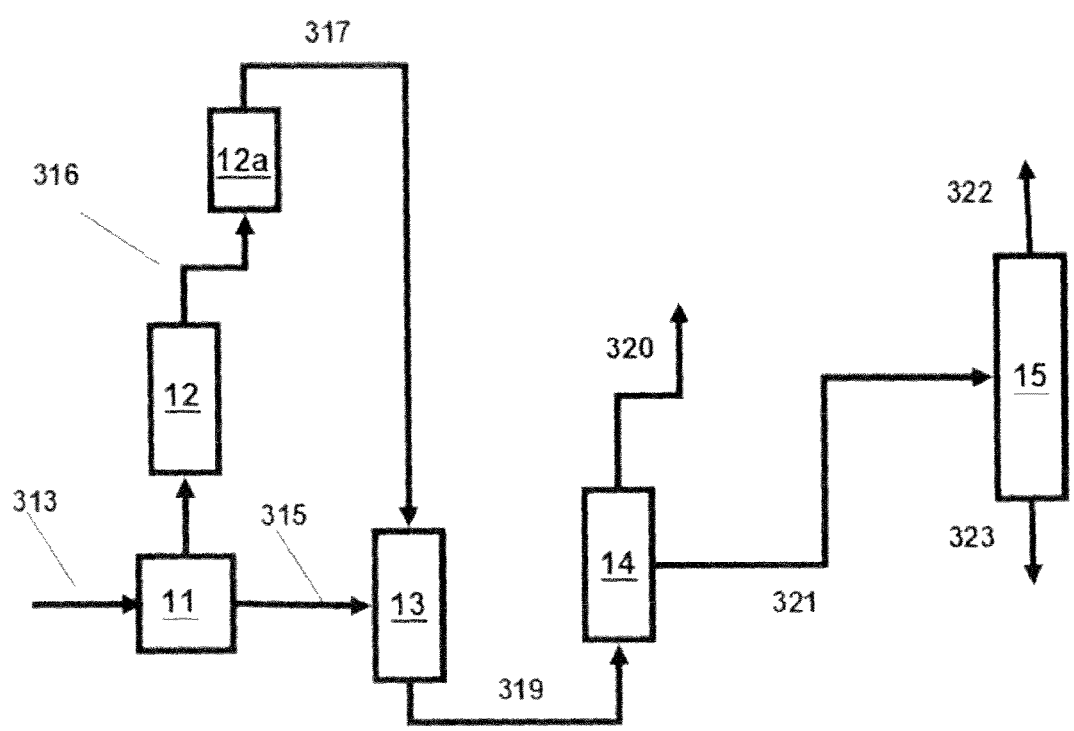
FIG. 2 is a flow sheet showing a work up process
Figure 3:
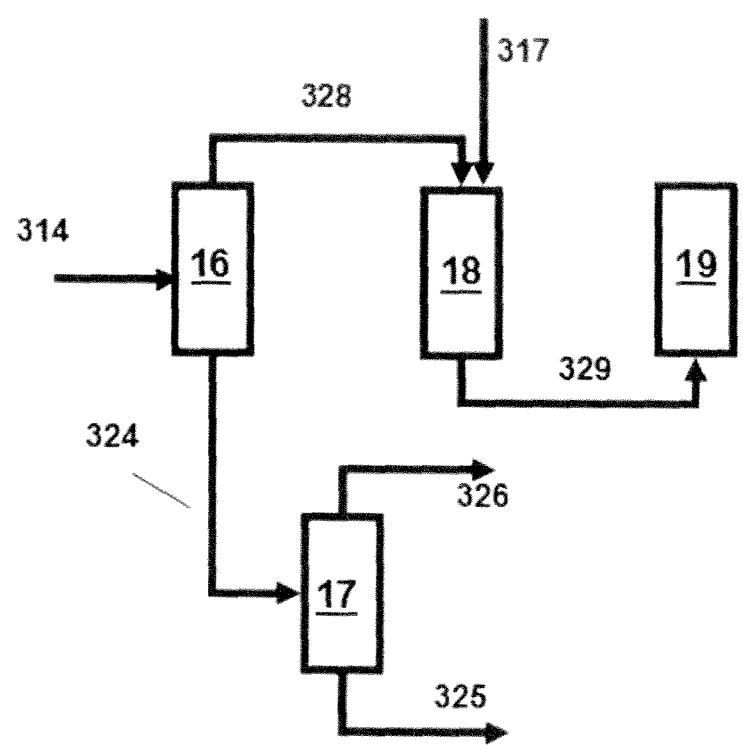
FIG. 3 is a flow sheet showing a further work up process

The plant comprises a dehydration reactor 1. Dehydration reactor comprises a catalyst bed over which ethanol is passed at high temperature. The dehydration of ethanol is endothermic and the catalyst bed needs to be heated. This is often achieved by heating the ethanol containing feed stream to above the desired catalyst reaction temperature. The precise nature of the catalyst and the temperature and pressure at which dehydration are undertaken are not of the essence of the invention. Typical conditions are well known to those skilled in the art and examples of suitable catalysts include heteropolyacids (HPA), zeolite and alumina. Typical temperatures for dehydration can be within range 200° C.-550° C. and pressures can range from 0.02 $MN/m^2$ to 4 $MN/m^2$ with optimum conditions defined by the catalyst type, desired ethanol conversion rate and product yields.

The material exiting the dehydration reactor 1 comprises ethylene but includes side products such as hydrogen, methane, carbon monoxide, aldehydes, butane, butene and heavier hydrocarbons plus low levels of oxygenates. Depending upon the catalyst used the material exiting the dehydration reactor may further comprise significant amounts of propylene as described for example in Catalysis Letters (2009) 131, 364-369. The material exiting the reactor via dehydration reactor conduit 300 is cooled via heat exchange in heat exchanger 2 with for example one or more of dehydration reactor feedstock, steam generation or pyrolysis furnace feedstock, then quenched with water at a temperature below 40° C. to condense the majority of water and a portion of reaction by-products. The overheads stream is thereafter optionally subject to a compression stage and then fed via washing tower inlet conduit 301 to washing tower 3 where it is washed with water at low temperature e.g. at about 30° C. for example 25 to 40° C. It has surprisingly been found that such a simple water wash removes aldehydes sufficiently effectively to prevent red oil formation in subsequent steps. If desired a caustic wash can be employed as well as or instead of the water wash. The crude ethylene is passed to a steam cracker cracked gas multistage compressor 4, preferably to a late stage such as the last stage of the compressor for compression by first compressor inlet conduit 302. A cracked gas compression train in steam cracking typically comprises a multistage compressor with inter-stage coolers to remove the heat generated during compression. Compressors can comprise typically 3, 4 or 5 stages of compression to compress gas from typically 0.03 $MN/m^2$ to 3.5 $MN/m^2$, with the caustic wash step located just prior to the last stage of compression. The crude ethylene addition point may be before or after the caustic wash treatment step of the cracked gas. Where the pressure of the material exiting the dehydration reactor is already at high pressure the quench stage and water wash stages described above are combined and no separate compression step is required before passing to compressor 4. Further processing of the compressed impure ethylene will be described later.

Meanwhile effluent from a steam cracker where naphtha is used as a typical feedstock is cooled in a first cooling tower 5. Fuel oil condenses in the first cooling tower 5 and is withdrawn through fuel oil outlet conduit 303. Material passing overhead the first cooling tower via first cooling tower outlet conduit 304 enters a second cooling tower 6. Heavy gasoline condenses and is withdrawn from the second cooling tower 6 through heavy gasoline outlet 305. The material passing overhead the second cooling tower 6 via second cooling tower outlet conduit 306 is passed to the multi-stage compressor 4 where it is compressed typically from <0.03 MN/m$^2$ to >3 MN/m$^2$ although as noted the dehydration reactor output generally enters a late stage of the compressor. Compression of the gas causes the medium gasoline to condense and it is collected via medium gasoline outlet 307. The output of the dehydration reactor is combined with the material passing through compressor 4 at an inter-stage cooling point at least after the 1$^{st}$ stage of compression and before the last stage. The remaining gaseous material is then passed via caustic tower inlet conduit 308 to a caustic tower 7 in which carbon dioxide and sulphur containing oxides and sulphides as well as low levels of oxygenates components e.g. acetaldehyde are removed, via reaction with differing strengths of sodium hydroxide before being passed through a water wash section. The cleaned gaseous output is then transferred to the final stage of compression thence via decanter inlet conduit 309 to decanter 8. Decanter 8 may be operated at a temperature provided by cooling water or may optionally be chilled to <20° C. using a refrigerant such as propylene for example. Condensed water is then removed by simple decantation in decanter 8 and is removed via water outlet 310. The remaining gaseous material is then passed by decanter outlet conduit 311 dried using molecular sieve drier 9 to remove residual water to a very low level typically of the order of less than 1 ppm. The dried material is passed via drier outlet conduit 312 to first distillation column 10 in which hydrogen, carbon monoxide and C1 and C2 fractions are separated from C3, C4 and light gasoline. The light fraction comprising hydrogen, carbon monoxide and C1 and C2 species exit the first distillation column 10 via C1 conduit 313. The heavy fraction comprising C3, C4 and light gasoline exits the first distillation column 10 via C3 conduit 314. The light fraction via C1 conduit 313 is passed to third tower 11 and cold box 12. C2 fraction comprising ethane, ethylene and acetylene are collected from the third tower 11 via C2 fraction conduit 315 and a light fraction principally containing methane and hydrogen exits the cold box 12 via conduit 316, into a hydrogen purification unit 12A, typically a pressure swing adsorption unit which generates a high purity hydrogen product via conduit 317 and a fuel gas residue via conduit 318. Optionally, a methanation unit could be used instead of a PSA wherein residual carbon monoxide is catalytically converted to methane allowing the H2/CH4 product stream to be used in hydrogenation reactors. The C2 fraction passing from the third tower 11 via C2 fraction conduit is passed to a C2 hydrogenation system 13 comprising one or more sequential catalytic exothermic reactors, heat exchangers and optionally as a last processing step a water removal drum containing a molecular sieve. Hydrogen for example from the cold box 12 via hydrogen conduit 317 is also passed to the catalytic reactors within system 13 where it reacts with low levels, typically in the range 0.8 to 1.5 wt %, of acetylene contained in the stream to form additional ethylene and ethane. It is not necessary for the hydrogen to be pure and it may contain some methane. The materials then comprise small amounts of hydrogen and methane, in a significantly ethane and, in large excess, ethylene stream. They are passed to demethaniser 14 via demethaniser feed conduit 319 where the hydrogen and methane are removed via demethaniser outlet conduit 320.

The mixed hydrogen and methane may be returned to the cold box 12 for separation. Finally the ethane and ethylene are passed by ethane/ethylene conduit 321 to splitter 15 operating typically between 1.8-2.2 MN/m$^2$ pressure and between −2° C. to −10° C. base temperature from which ethylene of required purity (typically that suitable for polymerisation) is withdrawn by ethylene conduit 322. The ethane can be recycled back as a feedstock for a pyrolysis furnace via ethane conduit 323. The ethylene can then be transformed into other materials. For example the ethylene can be subjected for example in known manner to produce polyethylene. The precise purity of the withdrawn ethylene will depend upon the precise operating conditions in the splitter, such as temperatures, pressures and reflux ratios as required by the application to which it is to be put. Those skilled in the art will be able to deduce for example by routine experimentation appropriate levels of purity obtainable.

The heavy fraction from the first distillation column 9 is passed along conduit 314 to a depropaniser 16 where it is split into a fraction comprising C4 and light gasoline and a fraction comprising propane, propylene and propyne. The C4 and light gasoline fraction by C4 and light gasoline conduit 324 is passed to a debutanizer 17 where it is split into light gasoline and butane, butene and butadiene. Light gasoline is led away by light gasoline conduit 325. Butane, butene and butadiene are led away via mixed C4 conduit 326 for further processing. Further processing may comprise extraction of butadiene. The propane, propylene and propyne fraction is passed via mixed C3 conduit 328 to a second C3 hydrogenation system 18, comprising one or more sequential catalytic exothermic reactors and heat exchangers where it is reacted with hydrogen, for example hydrogen recovered from the cold box 12 via hydrogen conduit 317. The propyne fraction can be substantially converted (>99%) preferentially to propylene but also to propane and heavier oligomers. The hydrogen may contain methane. A mixture of hydrogen, methane, propane and propylene emerges from the C3 hydrogenation system 18. It is passed via secondary demethaniser feed conduit 329 to secondary demethaniser 19 which separates it into two streams; the overheads one comprising methane and hydrogen which can be returned to the cold box 12 for separation and the bottoms one containing propane and propylene. Propane can be extracted from this latter stream by utilising a propylene splitter and recycled back as a feedstock for the cracker and propylene can be utilised in other ways for example in making polypropylene.

The gasoline produced in the process is subjected to hydrogenation to remove dienes which can cause gum to form. The hydrogenated product is then fractionated giving rise to a light cut principally composed of C5 species. This material can be transformed into motor spirit and/or isoprene can be extracted from it. The middle fraction is subjected to deep hydrogenation to remove olefins. Benzene is extracted for sale leaving a benzene raffinate. The heavy cut comprises C7+ species from which aromatics can be extracted and/or which can be used for motor spirit.

In an alternative arrangement especially in low pressure systems working at the order of 0.1 MN/m$^2$ (as compared to of the order of 2 MN/m$^2$) in the previously described embodiment the effluent from the dehydrator can be cooled and condensed in a quench tower and then compressed and cooled again before passing to an oxygenates removal column.

Figure 4:
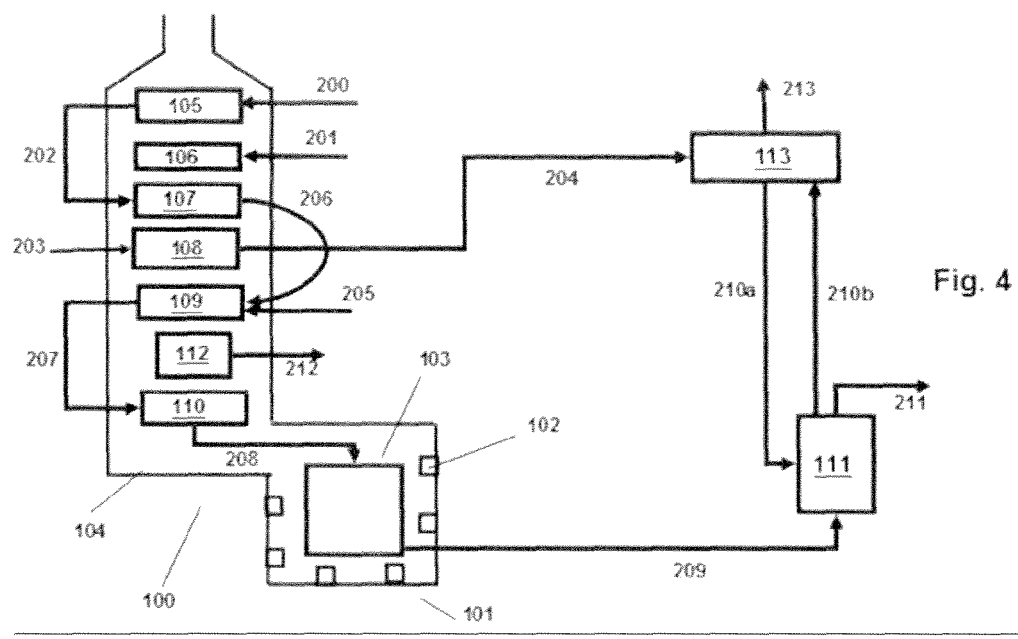
FIG. 4 is a schematic view of a furnace of the invention

An advantage of these arrangements is that co-products with ethylene, produced from the dehydration process such as C3, C4 compounds and ethane, can be economically recovered. In the case of an ethanol dehydration catalyst that produces predominately ethylene with only a small amount of co-products, the capacity of an existing steam cracker can be increased without increasing existing C3+ distillation section or C2 hydrogenation facilities. Only a minor impact on the compressor is envisaged due to compression stage loading changes. More ethylene is produced but this is a positive feature in that the ethylene is the main cooler in the cold box. Furthermore in a standalone ethanol dehydration scheme such as that described by Kochar et al in "Ethylene from Ethanol" as published in CEP June 1981 p 66-70 the hydrocarbon fractions produced from the dehydration catalyst such as the C4 hydrocarbons, propylene and ethane recovered as a Heavies purge in FIG. 4 is practically usable only as fuel gas component and amounts to approximately 1.5 mol % of the total product ex reactor being lost to a low value use. Where combined with a steam cracker as per the described embodiments of the invention the produced ethane can be recovered and used as a feedstock and thus be more valuable than when used as fuel gas and the other olefin fractions can be advantageously recovered as products.

Furthermore crackers often produce surplus fuel gas containing hydrogen. That gas can be optionally used to fuel a secondary furnace to provide additional heat for a dehydration unit not located within a pyrolysis furnace convection section leading to a smaller greenhouse gas (GHG) footprint than using a standalone methane fuelled dehydration unit. As a result the invention provides an improved energy balance and GHG footprint. Furthermore there may be a considerable economic benefit in at least some countries. Some countries especially those in Europe impose taxes on GHG emission. Imported ethanol contains considerable amounts of energy but since it is imported its contained energy will not incur a GHG emission tax penalty and dehydrating ethanol has a lower GHG footprint per to of ethylene than cracking conventional saturated hydrocarbons.

Desirably, but not essentially, the dehydration reactor is at least partially integrated with the steam cracker. For example the dehydration reactor can be heated by high pressure steam at temperatures in range 300° C.-520° C. generated in the pyrolysis furnace section of the steam cracker. In other embodiments of the invention however the dehydration reactor is more completely integrated into the cracker. This can be done in a new-build plant or by retro-fitting to an existing plant. As shown in FIG. 4 the dehydration reactor can be incorporated within the cracker pyrolysis furnace itself. Cracker 100 comprises a firebox 101 provided with at least one burner 102. Burners 102 may be floor and/or wall mounted in the firebox. Burners 102 are provided with fuel and air. At least part of the fuel can comprise materials obtained from the separation and purification system previously described.

Contained within the firebox are a plurality of pyrolysis tubes 103 to be described hereinafter in more detail. Combustion products leaving the firebox 101 enter convention section 104 where some otherwise waste heat can be recovered. The cooler end of the convection section 104 furthest from the firebox 101 is provided with a first preheater 105. Steam cracker feedstock such as naphtha or LPG enters the first preheater 105 through steam cracker feedstock conduit 200 and is heated by heat in the convection section 104. The convection section further comprises an ethanol preheater 106. Ethanol and water are passed into the convection section by ethanol feed conduit 201 and preheated in the ethanol preheater 106. Preheated steam cracker feedstock is passed to a second preheater 107 via first transfer conduit 202 where it is heated still further. While in the figure the first transfer conduit is shown as outside the convection section 104, it may however be inside the convection section. Water enters the convection section 104 via water feed conduit 203 and is preheated in a water preheater 108 in the convection section. It exits the convection section and passes to steam drum 113 via first steam drum feed 204 where it is heated in a manner to be described hereinafter and turned into high pressure saturated steam. Dilution steam enters via dilution steam conduit 205 and is mixed with preheated feedstock via first preheated feedstock conduit 206. Once again while first preheated feedstock conduit 206 is shown as outside the confines of the convection section 104 for the purposes of clarity, however it may be inside the convection section 104. Material exiting the third preheater, 109, passes to a fourth preheater 110, via second preheated feedstock conduit 207, where it is heated still further. From there the steam and feedstock mixture is passed to the pyrolysis tubes 103 in the firebox 101 via third preheated feedstock conduit 208. In the pyrolysis tubes 103 the cracker feedstock is heated to high temperature for a short period and converted into a wide range of species including hydrogen, methane, ethane, ethylene, acetylene, propylene, propane, propadiene, propyne, but-1-ene, but-2-ene, isobutene, butadiene, butane, isobutane and species which make up gasoline and fuel oil. The reactor effluent exits the pyrolysis tubes 103 via pyrolysis exit conduit 209 and enters transfer line exchanger 111 where it is rapidly cooled by transfer line exchanger coolant conduit 210$a$ connecting the steam drum 113 with the transfer line exchanger 111. The cooling fluid used to cool the reactor effluent is transferred back to the steam drum 113 via second steam drum feed 210$b$ where it exchanges heat with the water entering the steam drum 113 from the water preheater 108 to raise steam. The generated steam leaves steam drum 113 via conduit 213 for use elsewhere, for example elsewhere in the integrated process. The partially cooled reactor effluent is passed to a quench tower via quench tower feed conduit 211 after which it is subjected to the separation and purification steps previously described.

Meanwhile vaporised ethanol and water exiting the ethanol preheater 106 is passed to a dehydration reactor 112 situated in the convection section 104 via a dehydration reactor feed conduit (not shown). In an embodiment, high temperature and pressure steam from the steam drum may be optionally added to the ethanol containing stream leaving preheater 106 to provide additional heat energy and means of adjustment of the water to ethanol ratio to a desired value suitable for the chosen catalyst. The ethanol is heated and reacted in the presence of a catalyst using heat derived from the pyrolysis furnace flue gases to produce ethylene and water as hereinbefore described. The ethylene and water are led away from the dehydration reactor 112 to dehydration reactor outlet conduit 212 to be treated as herein before described.

It will be readily apparent to the skilled worker in the art that the invention is not limited to the particular embodiment described. The skilled worker will be able to devise many modifications especially in the pre-heat and separation arrangements. For example the described embodiment the cracker feedstock is naphtha that is vaporised before dilution steam is added. In other embodiments gas crackers fed with ethane, propane/butane mixtures or combinations of such gas feeds are used. The feed enters the pyrolysis furnace already vaporised and mixed with dilution steam. Thus embodiments using gaseous feedstock would have a different preheater configuration in order to achieve the necessary heat balances.

More than one pyrolysis furnace, for example two, three or four may be provided. At least one of the pyrolysis furnaces may be provided with more than one dehydration reactor, for example two, three or four dehydration reactors may be provided in a pyrolysis furnace. In a preferred embodiment there are four furnaces each provided with a single dehydration reactor. In addition, the inclusion of dehydration reactors within the furnace convection section as described in FIG. 4, in particular allows the ethanol dehydration reaction to be carried out isothermally allowing enhanced control of reaction conditions and product yields. The dehydration reactor can comprise a plurality of individual reactors which are arranged in series or in parallel or partly in series and partly in parallel. The reactor or reactors can comprise tubular reactors packed with catalyst. Preferably tubes have a length to diameter ratio greater than 5:1 such 10:1 up 20:1, 30:1, 40:1, 50:1 or more.

By including the ethanol dehydration reactor within the convection section of the steam cracker heat losses can be reduced.

Because the olefin purification steps require multiple distillation towers and refrigeration systems purification it is expensive and thus integration of the two ethylene production systems rather than the provision of a stand alone dehydration process as previously described by Teng or Kochar or Chematur Enginering Group allows both more value to be extracted from the dehydration reaction co-products, such as ethane and C4s, and a lower capital cost to generate more ethylene which is suitable for polymerisation applications than from expansion of a conventional steam cracker by the addition of conventional pyrolysis furnaces using naphtha or ethane as feedstock. This can be seen in more detail by comparison of FIGS. 5 and 6 which show losses of ethylene from a prior art dehydration reactor of the invention in comparison with losses from a dehydration reactor of the invention. It will of course be borne in mind that the invention is not limited to the particular arrangement described.

Figure 5:
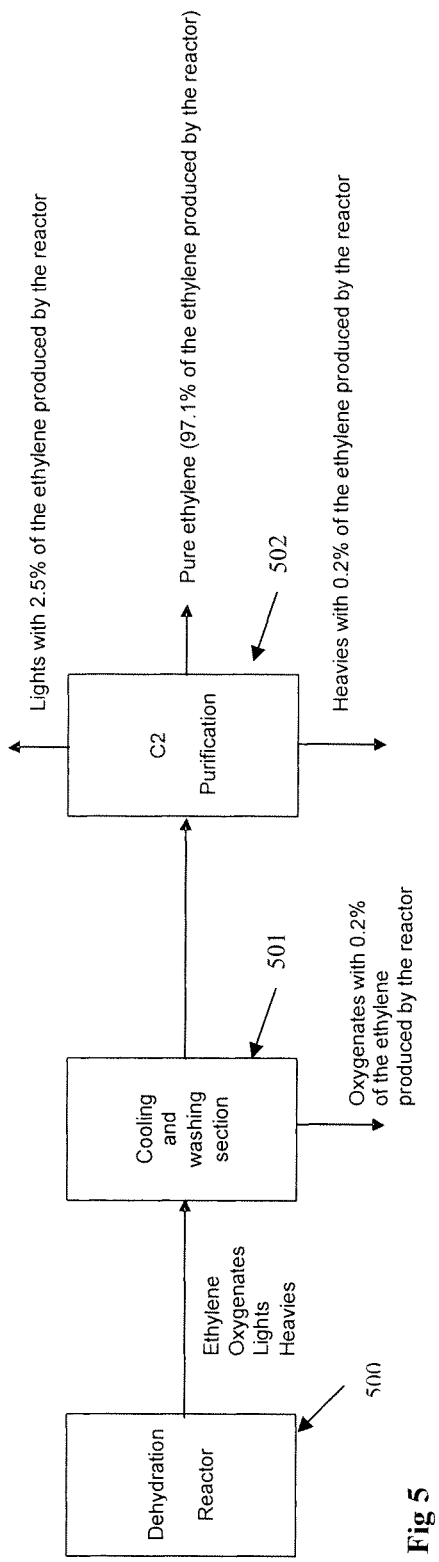
FIG. 5 shows losses of ethylene in a prior art standalone reactor and FIG. 6 shows losses of ethylene from a dehydration reactor used in accordance with the invention.

As can be seen from FIG. 5 the prior art dehydration reactor 500 produces ethylene together with oxygenates, lights and heavies. The crude product is washed to remove oxygenates in washer 501 and 0.2% of the ethylene is lost at this stage. The washed product is passed to a purifier 502 where it is separated into three fractions; a pure ethylene fraction, a lights fraction and a heavy fraction. At a particular purity of ethylene such as that suitable for polymerisation, 2.5% of the ethylene produced by the reactor was lost in the lights fraction and 0.2% was lost in the heavies fraction. Accordingly in total 2.9% of the produced ethylene was lost and only 97.1% recovered. Much of the lost ethylene could in principle be recovered but in practice it is not economic to do this due to it being a complex mixture of olefins and alkanes, because the cost of the recovery equipment outweighs the value of the recovered ethylene.

Figure 6:
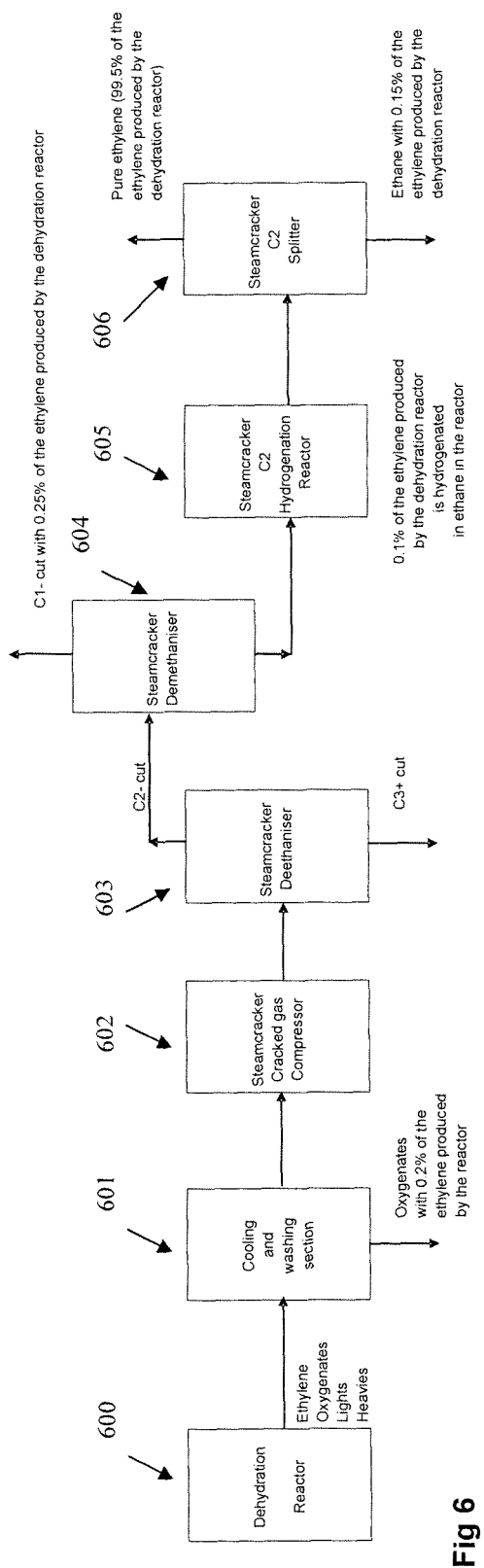

In accordance with the invention a dehydration reactor is integrated with a steam cracker. A steam cracker produces far less pure ethylene than a dehydration reactor. Accordingly it is both necessary and economical to have more advanced ethylene recovery plant in association with a steam cracker than with a dehydration reactor. Since the dehydration reactor product is so very high in olefin content it can be further purified using the purification system of a steam cracker with little or no upgrade requirement for the steam cracker purification system. As will be explained by reference to FIG. 6 this allows significant extra ethylene to be recovered. In FIG. 6 dehydration reactor 600 produces ethylene together with oxygenates, lights and heavies. The crude product is washed to remove oxygenates in washer 601 and 0.2% of the ethylene is lost at this stage. The washed product is processed as hereinbefore described. Specifically the washed product is passed to a steam cracker cracked gas compressor 602 and then to a steam cracker depropaniser 603 which splits the product into the C3-and-heavier cut and a C2-and-lighter cut. Substantially all the ethylene passes with the C2 cut. The C2 cut passes to a demethaniser 604 which removes the C1 fraction together with 0.25% of the ethylene produced in the dehydration reactor. The major ethylene containing fraction is then passed to a hydrogenation reactor 605 where 0.1% of the ethylene originally produced in the dehydration reactor is converted to ethane, based on typical acetylene hydrogenation catalyst performance and co hydrogenation of ethylene to ethane. The resulting mixture of ethylene and ethane is passed to a C2 splitter 606 where the ethylene is purified typically to the same degree as in the process described by reference to FIG. 5. 0.15% of the ethylene originally produced in the dehydration reactor is lost along with the ethane. In total therefore in accordance with the invention only 0.7% of the ethylene produced in the dehydration reactor is lost compared with 2.9% in the prior art stand alone scheme.

In addition to providing enhanced recovery of ethylene the invention can provide debottlenecking advantages.

The precise relative sizes of the two sources of ethylene are not critical. If the dehydration reactor is too small then the economic benefit of the invention may not be sufficiently attractive. If the dehydration reactor is too large then the volume of gas passing through the purification stages may be too great especially where the dehydration reactor is provided as an add-on to an existing cracker plant. In typical embodiments of the invention the cracker provides from 20 to 90% such as 30, 40, 50, 60, 70 or 80% of the total ethylene produced by the apparatus of the invention.

Example 1

The following tables illustrate the advantages described above when the invention is used to expand capacity of an existing naphtha steam cracker for the production of light olefins by an additional ethylene capacity of 75 kta. The example is for a predominately ethylene product being derived from an ethanol dehydration process generating an impure olefins stream of composition, as described in Table 1, available at the exit of the cooling and washing section 601 as illustrated in FIG. 6.

TABLE 1

Ethanol Dehydration process - impure washed olefins stream (dry basis)

| Product | Weight % |
| --- | --- |
| Hydrogen | 0.06 |
| Methane | 0.03 |
| Carbon Monoxide | 0.04 |
| Ethylene | 99.4 |
| Ethane | 0.2 |
| Propylene | 0.1 |
| Propane | 0.01 |
| C4's | 0.16 |

The above stream composition is derived from an ethanol reaction using three sequential adiabatic reactors incorporating a silica alumina catalyst located external to a pyrolysis furnace operating under conditions as described in Table 2. Feed ethanol is dry before being mixed with a recycle water stream recovered from the downstream quench cooling section which contains 0.6 wt % of recovered unreacted ethanol plus residual ppm levels of other hydrocarbons and oxygenates after initial water processing. In the case of this example the CO fraction is methanated in the steam cracker and recovered as part of the methane fraction in Table 3.

TABLE 2

Dehydration Reactor Conditions

| Condition | Reactor 1 | Reactor 2 | Reactor 3 |
|---|---|---|---|
| Inlet Temperature ° C. | 460 | 460 | 440 |
| Outlet Temperature ° C. | 378 | 335 | 344 |
| Proportion of fresh ethanol fed to reactor % | 30 | 35 | 35 |
| Pressure MN/m$^2$ | 1.92 | 1.91 | 1.9 |

The raw reactor products stream upon leaving the reactor is rich in ethylene and water vapour at the conditions described. The stream is cooled to <40° C. using recovery exchangers such as feed ethanol preheat exchangers and steam raising exchangers cooling water exchangers. Condensed liquids, predominately water, are withdrawn using various vessels from the cooled stream immediately after heat removal devices as per common engineering practice. The recovered water streams are combined, subjected to stripping for bulk hydrocarbon removal with the majority recycled to the dehydration reactor and excess subjected to wastewater treatment processes. The largely water depleted ethylene rich stream is then passed at elevated pressure into a caustic treatment unit for removal of acetaldehyde. The stream will still remain water saturated at the exit of this stage prior to combination with the 1$^{st}$ olefin stream from the steam cracker within the cracked gas compression train.

A proprietary process model that accurately reflects a typical steam cracker was used to derive the process flows for the cases considered. The invention was modelled using the data from Table 1 as a typical composition achievable from an ethanol dehydration reactor and treatment system prior to combining with a steam cracker generated olefins stream.

TABLE 3

Comparison of invention over conventional expansion options for 70 kta extra ethylene

| Typical Steam Cracker Products | Base Case - Naphtha feed (Prior Art) | Expansion Case 1 additional Naphtha Furnace (Comparative) | Expansion Case 2 additional Ethane Furnace (Comparative) | Expansion Case 3 Ethanol Reactor (Invention) |
|---|---|---|---|---|
| Hydrogen | 156 | 171 | 194 | 157 |
| Methane | 967 | 1080 | 960 | 966 |
| Ethylene | 2082 | 2296 | 2296 | 2296 |
| Propylene | 1335 | 1478 | 1139 | 1335 |
| Raw C4 | 949 | 1047 | 958 | 950 |
| PYGAS | 1854 | 2046 | 1860 | 1854 |
| RESIDUE | 109 | 122 | 109 | 109 |
| Losses | 30 | 32 | 30 | 30 |

All units are in te/d

In the base case naphtha is fed to a steam cracker. In Expansion Case 1 a further naphtha furnace is provided so as to produce a further 70 kta ie 214 te/d of ethylene. It will be seen that in addition to this desired material other less useful products are formed. For example a further 15 te/d hydrogen is produced along with a further 113 te/d methane. It will be recalled that in order to remove these materials the product has to be passed through cold box 12. Since the quantity of material passing through the cold box and requiring cooling is significantly increased it may well be necessary to upgrade the cold box as well as providing a further furnace. In like manner larger amounts of other materials are produced and need to be processed. Accordingly further upgrading of the system is required.

In Expansion Case 2 a further ethane furnace rated to produce a further 70 kta ethylene is provided. Expansion Case 2 is rather better than Expansion Case 1 in terms of many less preferred products such as methane but still larger amounts of hydrogen will be produced requiring greater cold box capacity. In addition, those skilled in the art of steam cracking will recognise that ethane conversion is not 100% and that subsequently typically approximately ⅓rd of the product by weight leaving an ethane furnace may be unreacted ethane which requires to be passed through compression and purification sections of the plant before being recycled back to the pyrolysis furnace. Processing this unconverted ethane leads to significant power and thermal duty requirements on the steam cracker.

In accordance with the invention, Expansion Case 3, an ethanol dehydration reactor producing a further 70 kta ethylene is provided. As can be seen from Table 3 while the greater amount of ethylene is produced the other materials are barely increased. This is due to the very selective conversion of the ethanol to ethylene as illustrated in table 1 and in particular the very low ethane yield which is a significant advantage over Case 2 in terms of much reduced ethane processing for recycle. Accordingly little or no upgrading of purification equipment is required in accordance with the invention resulting in lower capex and operating costs.

It can be seen from the above table that using ethanol as a cracker expansion feedstock via the embodiments of this invention achieves enhanced ethylene production with minimal increases or even decreases in unwanted side products and minimised recycle streams, such that fewer process units in the refrigerated olefin purification scheme will require to be expanded thus reducing overall cost of producing the additional olefin capacity.

The invention is not especially limited in the nature of the catalyst used to effect the dehydration of ethanol and the skilled worker will have no difficulty in selecting suitable catalysts to suit conditions of feedstock purity or product yield profile. In some embodiments however the catalyst is selected so as to produce appreciable amounts of propylene as well as ethylene. Examples of processes and catalysts which produce propylene include those described in WO2007/083241 and WO2007/055361. The so formed propylene can be recovered very economically giving rise to a process which provides a convenient and economic source of propylene from ethanol especially bioethanol.

The invention claimed is:

1. A method of producing ethylene and propylene comprising:
   a) subjecting a feedstock to steam cracking in a steam cracker having a cracker pyrolysis furnace to produce a first olefin containing stream;
   b) heating an ethanol containing stream with heat from the cracker pyrolysis furnace;
   c) passing the heated ethanol containing stream over a dehydration catalyst at a temperature between 200° C. to 500° C. to produce a second olefin containing stream comprising aldehydes, and treating the second olefin containing stream to reduce the aldehyde content thereof prior to combination with the first olefin containing stream;

d) combining the first olefin containing stream and second olefin containing stream to give an initial product stream comprising ethylene and propylene; and e) subjecting the initial product stream to purification comprising at least:
   i) water content reduction;
   ii) hydrogen content reduction;
   iii) reduction of content of molecules containing 4 or more carbon atoms; and
   iv) ethane content reduction.

2. The method of claim 1 wherein the ethylene is separated from the propylene.

3. The method of claim 1 wherein the water content is reduced by cooling the initial product stream to a temperature below 20° C. so as to produce liquid water which can be separated from the initial liquid stream.

4. The method of claim 1 wherein the hydrogen content reduction comprises at least one means selected from the group consisting of a pressure swing absorber, palladium membrane, platinum membrane and cryogenic distillation column.

5. The method of claim 1 wherein the content of molecules containing 4 or more carbon atoms is reduced using a distillation column.

6. The method of claim 1 wherein the ethane content reduction comprises cooling the initial product stream using a cooler and directing the initial product stream to a distillation column to obtain an ethylene rich ethane poor fraction and an ethylene poor ethane rich fraction.

7. The method of claim 1 wherein at least one of the first olefin containing stream and the second olefin containing stream are additionally subject to water content reduction prior to combination.

8. The method of claim 1 wherein in step e) the water content of the initial product stream is reduced to less than 10 ppm (by volume at STP), the ethane content of the initial product stream is reduced to less than 500 ppm (by volume at STP), the hydrogen content of the initial product stream is reduced to less than 10 ppm (by volume at STP) and the content of molecules containing 4 or more carbon atoms is reduced to less than 10 ppm (by volume at STP).

9. The method of claim 1 wherein the first and second olefin streams are combined within a compression stage of a compressor at a pressure within the range 0.15 MN/m2 to 3.5 MN/m2.

10. The method of claim 9 wherein the first and second olefin streams are combined in between the 1st and last stage of a multistage compressor.

11. The method of claim 9 wherein the first and second olefin streams are combined in between the 1st and 5th stages of a multistage compressor.

12. The method of claim 9 wherein the first and second olefin streams are combined in between the 1st and 4th stages of a multistage compressor.

13. The method of claim 9 wherein the first and second olefin streams are combined within the compressor and prior to a caustic washing step.

14. A method of preparing a polymer of ethylene comprising the steps of
   a) preparing ethylene by the method of claim 1 and
   b) polymerising it.

15. A method as claimed in claim 14 wherein the ethylene is polymerised in the presence of at least one other polymerisable monomer.

16. Apparatus for producing ethylene and propylene by the method of claim 1, the apparatus comprising
   i) a steam cracker for cracking a feedstock to produce a first olefin containing stream, the steam cracker comprising at least one cracker pyrolysis furnace for heating the feedstock and for heating steam to produce at least one of ethylene and propylene with each furnace incorporating a convection section for recovering heat in the flue gas exiting the combustion section of the pyrolysis furnace;
   ii) a dehydration reactor for dehydrating ethanol to produce a second olefin containing stream situated within a cracker pyrolysis furnace of the steam cracker;
   iii) means for combining the first and second olefin containing streams to produce an initial product stream; and
   v) purifying means for purifying the initial product stream to produce a final product stream comprising ethylene the purifying means comprising at least
      1) a cooler for cooling the initial product stream to a temperature below 20 C so as to produce liquid water which can be separated from the initial liquid stream;
      2) means for separating at least some hydrogen from the initial product stream selected from the group consisting of a pressure swing absorber, palladium membrane, platinum membrane and a cryogenic distillation column for separating at least some hydrogen from the initial product stream;
      3) a distillation column for removing at least some molecules containing 4 or more carbon atoms from the initial product stream; and
      4) a cooler for cooling the initial product stream and a distillation column arranged to give an ethylene rich-ethane poor fraction and an ethylene poor-ethane rich stream and for separating the ethylene rich-ethane poor stream from the ethylene poor ethane-rich stream.

17. Apparatus as claimed in claim 16 further comprising a molecular sieve drier downstream of the cooler 1) for removing further water from the initial product stream.

18. Apparatus as claimed in claim 16 further comprising means for reducing the aldehyde content of the second olefin containing stream before combination with the first olefin containing stream.

19. Apparatus for producing a polymer of ethylene the apparatus comprising apparatus for preparing ethylene and propylene as claimed in claim 14 and a reactor for polymerising the ethylene.

* * * * *